United States Patent [19]

Schoolman

[11] Patent Number: 5,488,952
[45] Date of Patent: Feb. 6, 1996

[54] STEREOSCOPICALLY DISPLAY THREE DIMENSIONAL ULTRASOUND IMAGING

[75] Inventor: Arnold Schoolman, Kansas City, Mo.

[73] Assignee: Schoolman Scientific Corp., Kansas City, Mo.

[21] Appl. No.: 250,933

[22] Filed: May 31, 1994

Related U.S. Application Data

[63] Continuation of Ser. No. 91,452, Jul. 14, 1993, abandoned, which is a continuation of Ser. No. 615,216, Nov. 19, 1990, abandoned, which is a continuation-in-part of Ser. No. 334,706, Apr. 6, 1989, abandoned, which is a continuation-in-part of Ser. No. 229,472, Aug. 8, 1988, abandoned, which is a continuation-in-part of Ser. No. 179,059, Apr. 8, 1988, abandoned, which is a continuation-in-part of Ser. No. 935,066, Nov. 21, 1986, Pat. No. 4,737,972, which is a continuation of Ser. No. 671,436, Nov. 14, 1984, abandoned, which is a continuation-in-part of Ser. No. 616,385, Jun. 1, 1984, Pat. No. 4,559,555, which is a continuation-in-part of Ser. No. 351,917, Feb. 24, 1982, abandoned.

[51] Int. Cl.$^6$ .............................. G03C 9/08; A61B 8/00
[52] U.S. Cl. .................................... 178/660.070; 128/916
[58] Field of Search ...................... 364/413.22, 413.25; 348/42, 51, 53, 46; 128/660.04, 916, 653.1, 660.01, 660.05; 351/201

[56] References Cited

U.S. PATENT DOCUMENTS

| | | |
|---|---|---|
| 2,995,156 | 10/1960 | Heilig . |
| 3,670,097 | 6/1972 | Jones . |
| 3,705,261 | 12/1972 | Langley ........................ 348/42 |
| 3,783,282 | 1/1974 | Hoppenstein ................ 378/41 |
| 3,794,738 | 1/1974 | Natter . |
| 3,829,838 | 8/1974 | Lewis et al. ................. 395/119 |
| 3,840,747 | 10/1974 | Macovski ..................... 250/369 |
| 3,873,834 | 3/1975 | Dammann et al. ........... 378/23 |
| 3,883,689 | 5/1975 | Mansour et al. . |
| 3,919,475 | 11/1975 | Dukiek et al. . |
| 3,923,370 | 12/1975 | Mostrom . |
| 3,940,204 | 2/1976 | Withrington . |
| 3,949,229 | 4/1976 | Albert ........................... 378/98.6 |
| 3,976,840 | 8/1976 | Cleveland et al. . |
| 4,028,725 | 6/1977 | Lewis . |

(List continued on next page.)

FOREIGN PATENT DOCUMENTS

| | | |
|---|---|---|
| 0088356 | 9/1983 | European Pat. Off. . |
| 6180457 | 4/1986 | Japan . |
| 0080457 | 8/1986 | Japan . |
| 451980 | 8/1936 | United Kingdom . |
| 1254753 | 11/1971 | United Kingdom . |
| 2113058 | 7/1983 | United Kingdom . |
| WO8302706 | 8/1983 | WIPO . |
| WO8304155 | 11/1983 | WIPO . |
| WO8401680 | 4/1984 | WIPO . |

OTHER PUBLICATIONS

Aviation Week & Space Tech., Oct. 11, 1983; p. 133, (Vimad device).

An Intro to Physics of Diag. Rad; Christensen et al., 2nd Ed. 1978 Chp 19, pp. 276–277.

*Primary Examiner*—Gail O. Hayes
*Assistant Examiner*—Joseph Thomas
*Attorney, Agent, or Firm*—Litman, McMahon and Brown

[57] ABSTRACT

A stereoscopically displayed three dimensional ultrasound imaging system derives image data from an ultrasound imaging apparatus including a two dimensional ultrasound transducer array, reconstructs the image data into a three dimensional model, and displays right and left stereoscopic three dimensional image components of the model on corresponding right and left video display devices of a stereoscopic viewing unit. The system includes a system computer interfaced to the imaging apparatus and a pair of image channels, each including a three dimensional display processor, and a video display device. The three dimensional display processors receive polygon image data, reconstruct it into a three dimensional form, and select image data representing a three dimensional view from a selected perspective. The system computer controls the display processors to present mutually angularly displaced views of the same three dimensional image to form the stereoscopic image components.

31 Claims, 6 Drawing Sheets

U.S. PATENT DOCUMENTS

| | | | |
|---|---|---|---|
| 4,034,401 | 7/1977 | Mann . | |
| 4,051,534 | 9/1977 | Dukick et al. . | |
| 4,052,888 | 10/1977 | Brown et al. | 73/625 |
| 4,057,745 | 11/1977 | Albert | 378/137 |
| 4,115,802 | 9/1978 | Kramer et al. . | |
| 4,153,913 | 5/1979 | Swift . | |
| 4,160,263 | 7/1979 | Christy et al. . | |
| 4,214,267 | 7/1980 | Roese et al. | 378/42 |
| 4,242,703 | 12/1980 | Tsuboshima et al. . | |
| 4,246,607 | 1/1981 | Vijveberg . | |
| 4,247,908 | 1/1981 | Lockhort, Jr. et al. . | |
| 4,266,271 | 5/1981 | Chamoff et al. . | |
| 4,277,837 | 7/1981 | Stuckert . | |
| 4,310,849 | 1/1982 | Glass | 358/88 |
| 4,345,315 | 8/1982 | Cadotte et al. . | |
| 4,360,875 | 11/1982 | Behske . | |
| 4,398,799 | 8/1983 | Swift . | |
| 4,434,799 | 3/1984 | Taenger . | |
| 4,436,684 | 3/1984 | White . | |
| 4,437,348 | 3/1984 | Saski . | |
| 4,442,842 | 4/1984 | Baba . | |
| 4,457,311 | 7/1984 | Sorenson et al. . | |
| 4,472,737 | 9/1984 | Iwasaka . | |
| 4,475,104 | 10/1984 | Shen . | |
| 4,485,626 | 12/1984 | Ohhashi | 364/413.16 |
| 4,509,043 | 4/1985 | Mossaides . | |
| 4,521,688 | 6/1985 | Yin | 250/363.04 |
| 4,523,226 | 7/1985 | Lipton et al. | 348/49 |
| 4,559,555 | 12/1985 | Schoolman | 358/88 |
| 4,627,087 | 12/1986 | Marks . | |
| 4,647,966 | 3/1987 | Phillips et al. | 348/58 |
| 4,651,201 | 3/1987 | Schoolman . | |
| 4,672,649 | 6/1987 | Rutt | 378/10 |
| 4,677,299 | 6/1987 | Wong . | |
| 4,677,337 | 6/1987 | Klemschmidt . | |
| 4,692,878 | 9/1987 | Ciongoli | 395/119 |
| 4,710,002 | 12/1987 | Pomerantzeff | 351/205 |
| 4,710,876 | 12/1987 | Clini et al. . | |
| 4,719,585 | 1/1988 | Clini et al. . | |
| 4,734,756 | 3/1988 | Butterfield et al. | 348/43 |
| 4,737,921 | 4/1988 | Goldwasser et al. . | |
| 4,737,972 | 4/1988 | Schoolman . | |
| 4,747,411 | 5/1988 | Ledley . | |
| 4,798,210 | 1/1989 | Ledley | 128/600.1 |
| 5,122,650 | 6/1992 | McKinley | 250/208.1 |
| 5,191,203 | 3/1993 | McKinley | 250/208.1 |

(PRIOR ART)

STEREOSCOPICALLY DISPLAY THREE DIMENSIONAL ULTRASOUND IMAGING

CROSS-REFERENCE TO RELATED APPLICATIONS

The present application is a continuation of application Ser. No. 08/091,452, filed Jul. 14, 1993, now abandoned, which is a continuation of application Ser. No. 07/615,216, filed Nov. 19, 1990, now abandoned, which is a continuation-in-part of Ser. No. 07/334,706 filed Apr. 6, 1989, now abandoned which is a continuation-in-part of Ser. No. 07/229,472 filed Aug. 8, 1988 for STEREOSCOPICALLY DISPLAYED THREE DIMENSIONAL MEDICAL IMAGING now abandoned, which is a continuation-in-part of Ser. No. 07/179,059 filed Apr. 8, 1988 for HIGH FIDELITY STEREOSCOPIC COMBINED LCD AND CRT TELEVISION DISPLAY, now abandoned, which is a continuation-in-part of Ser. No. 06/935,066 filed Nov. 21, 1986 for STEREOSCOPIC FLUOROSCOPE ARRANGEMENT, now U.S. Pat. No. 4,737,972, which is a continuation of Ser. No. 06/671,436 filed Nov. 14, 1984, abandoned, which is a continuation-in-part of Ser. No. 06/616,385 filed Jun. 1, 1984 for STEREOSCOPIC REMOTE VIEWING SYSTEM, now U.S. Pat. No. 4,559,555, which is a continuation-in-part of Ser. No. 06/351,917 filed Feb. 24, 1982 for PORTABLE REMOTE TERMINAL WITH HEAD HELD DISPLAY, abandoned, all such applications being incorporated herein by reference.

FIELD OF THE INVENTION

The present invention relates to improved medical image display methods and apparatus and, more particularly, to methods and apparatus for three dimensional imaging of anatomical structures and stereoscopically displaying image data derived thereby.

BACKGROUND OF THE INVENTION

Physicians have a need for knowledge and information of the structure and condition of a patient's internal anatomy. More importantly, physicians have a need for such information which may be obtained, when possible, by noninvasive techniques, that is, non-surgically. These needs were first addressed by the use of x-rays or radiographs. In recent years, however, the x-ray machine has been supplemented in many situations by medical imaging techniques which yield information in orientations which are not easily imaged by traditional x-rays and in three dimensions (3D). These techniques include, for example, computed tomography, magnetic resonance imaging, positron emission tomography, tomographic gamma scintillation imaging, and ultrasound scanning.

Perhaps the best known technique of this type is computed tomography (CT), also known as computed axial tomography (CAT). With computed tomography, a complete three dimensional examination is made up of a sequence of two dimensional (2D) cross sections or "slices". Slice information is acquired by rotating a thin, fan shaped beam of x-rays about the long axis of the patient. Each slice is irradiated by its edges; the transmitted x-ray beams are captured with position sensitive radiation detectors and, thus, x-ray attenuation measurements are obtained from many different directions across the slice. The two dimensional images are reconstructed from these measurements by a mathematical procedure known as convolution and back projection. The output of the reconstruction procedure is an array of numbers (known as picture elements or pixels in 2D and volume element or voxels in 3D) representing the radiological density (x-ray attenuation) at points within the slice.

A recently developed imaging modality which does not employ x-rays is magnetic resonance imaging (MRI). This technique uses large magnetic fields to excite protons within the body through the phenomenon of nuclear magnetic resonance (NMR). The excited protons produce a radio frequency (RF) signal which can be position encoded. Three dimensional information can be built up slice by slice, as with x-ray CT. The two dimensional slices are reconstructed for viewing using mathematical procedures analogous to those used in x-ray CT. In MRI, the information associated with each voxel is a composite of proton density (essentially, the amount of water present) and so called T1 and T2 relaxation times, which are functions of physical and chemical structure.

Other three dimensional imaging techniques fall within the realm of nuclear medicine. The basic principle here is to introduce radioactive substances (radio pharmaceuticals) into the body, relying on their pharmacological properties for uptake into specific organs (for example, radioactive iodine can be used to label the thyroid). These radioactive substances produce radiation which may be measured with position sensitive detectors external to the body, known as gamma cameras. Two dimensional projected images (comparable to those obtained with conventional x-rays) can be generated with analog electronic circuitry. To obtain reliable three dimensional information, however, single photon emission computed tomography (SPECT) or positron emission tomography (PET) is employed, both of which rely on digital techniques.

SPECT systems make use of routine gamma radiation emitting radiopharmaceuticals combined with tomographic scanning techniques and may be thought of as a tomographic gamma scintillation imaging technique. PET systems, in contrast, employ annihilation coincidence detection to detect positron annihilation radiation from positron emitting radiopharmaceuticals. In both of these modalities, the information associated with each voxel is a measure of the concentration of the radiopharmaceutical at the corresponding volume increment within the patient. SPECT and PET differ from CT and MRI in that the images are fundamentally physiological rather than anatomical (although certain MRI studies have a physiological component). Thus, for example, nuclear medicine studies are used to demonstrate abnormal growth activity in bones which otherwise appear normal.

Another common imaging modality which yields three dimensional information in digital format is diagnostic ultrasound. This technique relies on the reflection of sound waves at interfaces within the body (e.g., between fluid and soft tissue) to generate echoes; the elapsed time between the transmission of a pulsed sound wave and the reception of its echo gives a measure of the distance to the interface between types of tissue while the amplitude of the echo gives a measure of the difference in the material characteristics at an interface. Conventional ultrasound images are formed as slices in a manner analogous to CT. Digital techniques are not needed to produce the images although almost all modern devices store the image in digital format to avoid electronic drift and to facilitate post processing.

A major drawback of each of the imaging devices described above is that images are produced which comprise two dimensional slices of the internal anatomical structures being observed. Physicians must then mentally "stack" an entire series of these two dimensional slices in order to infer the structure of the three dimensional objects under investigation. Many problems are inherent in such an approach.

First, the interpretation of a series of stacked, two dimensional images by a physician requires a great deal of specialized knowledge and skill. Secondly, such an approach is extremely time consuming. Thirdly, the approach is prone to inaccuracy.

What is clearly needed is a medical display device which produces a three dimensional representation of internal anatomical structures produced from a full series of stacked two dimensional slices of that structure. Even more desirable is a medical image display device which provides the physician or other observer with the ability to manipulate the object and its image interactively in real time such that the object may be viewed from various directions and in various modes in real time. By real time display is meant that the video display output should be updated at or near video rates of 30 frames per second. Provided there is minimal or no delay between operator action and the corresponding charge in the final image, this update rate would provide instantaneous perceptual feedback. It should be clear that such an interactive three dimensional display system permitting a physician to visualize and interact with a shaded three dimensional representation of an anatomical structure would greatly facilitate the examination of the structure in conjunction with medical research, clinical diagnoses, and the planning and execution of treatment and surgical procedures.

A number of three dimensional display systems for medical objects have been described in the literature, but none of these provide realistic shaded images at the full resolution of the input data with real time interactive capabilities.

Three dimensional medical data sets can be displayed in the following ways: the data can be organized into a sequence of reprojected views or slices; it has been proposed to create true three dimensional images in space; and so-called two and a half dimensional (2.5D) images can be generated by projecting objects or object onto a two dimensional screen with depth cues given by shading.

Many computed tomography and magnetic resonance imaging display systems provide facilities to work through a sequence of two dimensional slices fairly rapidly, so that a trained physician can create a mental impression of the three dimensional structure. On the other hand, only the original slices captured by the imaging apparatus can be rapidly displayed. Reslicing or reformatting the image data to generate new two dimensional slices without re-imaging the patient, referred to as multi-planar reconstruction or MPR, slows the display process considerably.

True three dimensional images can be created in space using several different approaches. In one approach, a varifocal mirror is used to view slice images which are sequentially displayed on a cathode ray tube (CRT) under computer control. The mirror surface is vibrated in synchronism with the updating of the CRT. Different images are seen as the mirror vibrates back and forth, giving a sense of depth. Another proposed approach employs a volume of a fluorescent gas, such as iodine-chlorine (I—Cl) vapor, which is excited to fluorescence by intersecting laser beams. The laser beams are scanned in a similar manner to the raster scanning of video monitors and television screens, except in a three dimensional sense.

The most familiar method of generating realistic images from a three dimensional scene is to project it onto a two dimensional screen and rely on motion parallax, projective geometry, shading, and hidden surface removal to create the illusion of depth. The result is similar to conventional television and motion pictures, which viewers readily intrepret as representing three dimensional scenes.

Ultrasound imaging is a particularly useful technique in terms of noninvasiveness, safety and convenience to the physician and patient, and real time imaging capability. It is generally held that the ultrasound energy causes no discomfort or injury to the patient. In fact, ultrasound imaging is routinely used for imaging developing fetuses. As far as convenience, the physician simply positions the ultrasound transducer element or element array on the patient by hand and observes a cathode ray tube display of the image. This contrasts with other imaging techniques such as computed tomography and magnetic resonance imaging in which the patient is positioned in a large machine, out of immediate touch with the physician.

A major problem with ultrasound imaging is the low quality of the images provided thereby. "B mode" ultrasound images are formated in a manner somewhat similar to video images, that is, as repeated frames formed of image lines. Each line may represent the timing and amplitude of echoes resulting from a single pulse or firing of an ultrasound transducer or transducer element of an ultrasound array. Increasing the ultrasound pulse repetition rate increases the amount of image information available and, thus, increases the resolution of the resulting image. However, the maximum pulse repetition rate is limited by the speed of ultrasound energy travelling through various types of tissue After an ultrasound transducer element is "fired" it must be switched to receive mode to wait for returning reflections. Otherwise, outgoing pulses would overlap returning pulses which would complicate measurement of the depth of reflecting surfaces. In general, the maximum usable pulse repetition rate is inversely related to the thickness or depth of the organ or body part to be imaged with larger parts, such as the abdomen, requiring relatively low pulse repetition rates while smaller parts, such as the eye, allow higher rates.

To an extent, a trade-off can be made between the number of lines per images and the frame repetition rate. This allows more lines per frame at the expense of frame rate for a given pulse repetition rate. However, decreasing the frame rate diminishes the ability to image motion in real time. The lower limit for the frame rate is the rate at which image flicker begins to occur, which adversely affects viewability of the image.

Another factor which affects image quality is the problem of differentiating various types of soft tissue. Reflections of ultrasound energy from interfaces between different kinds of materials are caused by differences in the acoustic impedances of the materials. An interface between soft tissue and bone is relatively easy to image because of their significantly different acoustic impedances. In contrast, most types soft tissue have acoustic impedances which are not significantly different from that of water. Thus, reflections from an interface between two different types of soft tissue will be relatively weak and might be masked by system noise.

Even when relatively good ultrasound images can be obtained, recorded, and played back, it is still sometimes difficult to integrate a plurality of image slices into a three dimensional picture of the body region being imaged.

SUMMARY OF THE INVENTION

The present invention is a stereoscopic ultrasound system for medical imaging purposes which maintains many of the advantages of conventional ultrasound imaging and adds features which improve the quality of ultrasound imaging and the diagnostic capabilities thereof. In general, the stereoscopic ultrasound system of the present invention includes a two dimensional ultrasound transducer array, an ultrasound computer including transducer driver and detector circuitry to derive image data by measuring parameters of reflected ultrasound energy and spatial data related to the locations from which the reflections originate, a stereoscopic three dimensional imaging computer to reconstruct three dimensional models of the image data from multiple ultrasound slices from two stereoscopically related angles, and a stereoscopic display device for viewing the stereoscopic views of the three dimensional models.

The two dimensional transducer array may be thought of as a plurality of linear arrays of transducer elements positioned in fixed relation. The elements are activated in groups in timed relation to focus and steer ultrasound beams to scan the body part in slices. The array is preferably supported in such a manner that it can be moved and its relationship to previously imaged slices sensed. By this means, a sequence of groups of slices may be taken to image organs and body parts larger than the boundaries of the array itself. Such array support apparatus may include an articulated arm with position sensors at the joints thereof, a motorized patient platform, or the like.

The system of the present invention comprises a pair of parallel image channels, one for the right stereoscopic image component and one for the left component. Each image channel includes a three dimensional display processor which reconstructs ultrasound image data to form a three dimensional model of the anatomical structures of interest and selects the required data to display the structures represented by the image data from a selected viewpoint or perspective; a clipping and projection selector which selects the desired clip plane to eliminate data points on one side of the plane; a frame buffer or buffers for storing overlapping images; video display electronics including a color look-up table for selective shade control; and a video display device, such as a cathode ray tube. The operation of the 3D display processors is controlled and coordinated by a system computer to select display perspectives which are angularly displayed sufficiently for a stereoscopic impression to be created by the displayed image components. The system computer additionally derives polygon lists from image data in an image data storage medium or archive or directly from an ultrasound imaging apparatus and forwards the polygon lists to the right and left image channels.

The system computer of the stereoscopic imaging system includes a system memory, system mass storage devices and imput devices, such as a keyboard and a screen location selection or pointing device such as a mouse or trackball. The system memory and mass storage devices store the operating software for the system computer and may also store the operating software for the 3D display processors.

The software preferably includes a polygon generator and interpolator of the type disclosed in U.S. Pat. No. 4,710,876 to Cline et al. In this system, a polygon list is generated which represents a three dimensional cross-section of the ultrasound image. The polygon list is then sent to a conventional three dimensional display processor where routines such as rotation, magnification, color selection, data range deletion, etc., are performed. In the present invention, two identical display processors are provided, one for the left display channel and one for the right display channel. Identical polygon lists are supplied to each display processor and a viewing angle is selected through the system computer. The left and right images are offset by an angle calculated to simulate left and right eye views and the display processors then use these views.

Each display processor is a substantially conventional 3D image processor. Positional and normal vector information is received from the system computer. A viewing angle and viewing elevation are input as well as clipping information, shading control, etc. The resulting image is that of a 3 dimensional ultrasound image of a selected tissue type at the selected viewing angle. Hidden surfaces are removed via a conventional painter's algorithm. The display processors are synchronized via a common synchronizing signal derived from the master clock of the system computer. Such display processors are more particularly described in U.S. Pat. No. 4,719,585 granted Jan. 12, 1988 to Cline et al., which is hereby incorporated by reference.

It is foreseen that the video display devices may be developed in the future which equal cathode ray tubes in resolution and color quality. For such video devices, the display processors would provide appropriate signal formats. At least one of the display processors has an output for a large video monitor external to the stereoscopic viewing unit for viewing by groups of practitioners.

OBJECTS OF THE INVENTION

The principal objects of the present invention are: to provide an improved medical imaging system; to provide such a system which significantly improves the ability of physicians to substantially noninvasively diagnose diseases and anomalies of and injuries to internal organs and anatomical structures and to plan treatment and surgical procedures in relation thereto; to provide particularly a stereoscopically displayed three dimensional ultrasound imaging system; to provide such a system which enhances the realism of medical images particularly with regard to relative location of components of the images; to provide such a system which provides a stereoscopic display of image data of anatomical structures obtained as data representing a plurality of tomographic or cross sectional type images of a patient; to provide such a system including a pair of three dimensional display processors to simultaneously process image data representing angularly displaced right and left stereoscopic components of a three dimensional image and display the stereoscopic components on corresponding right and left video display devices of a stereoscopic viewer; to provide such a system in which the right and left video display devices are mounted in a head worn harness; to provide such a system including a system computer to control and coordinate the right and left three dimensional display processors, derive polygon lists from image data in an image data storage medium or directly from an ultrasound imaging apparatus and forward the polygon lists to the pair of display processors; to provide such a system with image manipulating capabilities such as rotations about selected axes, removal of selected parts of images, and the like; to provide such a system with image enhancement capabilities such as the assignment of gray scales or shades of colors to image portions derived from selected data value ranges and the interpolation or averaging between and among adjacent data points for apparent increases in displayed image resolution; to provide such a system which, with sufficient imaging apparatus and computer throughput, can process image data in substantially real time; and to provide such a stereoscopically displayed three dimensional ultrasound imaging system which is economical to manufacture, precise in operation, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
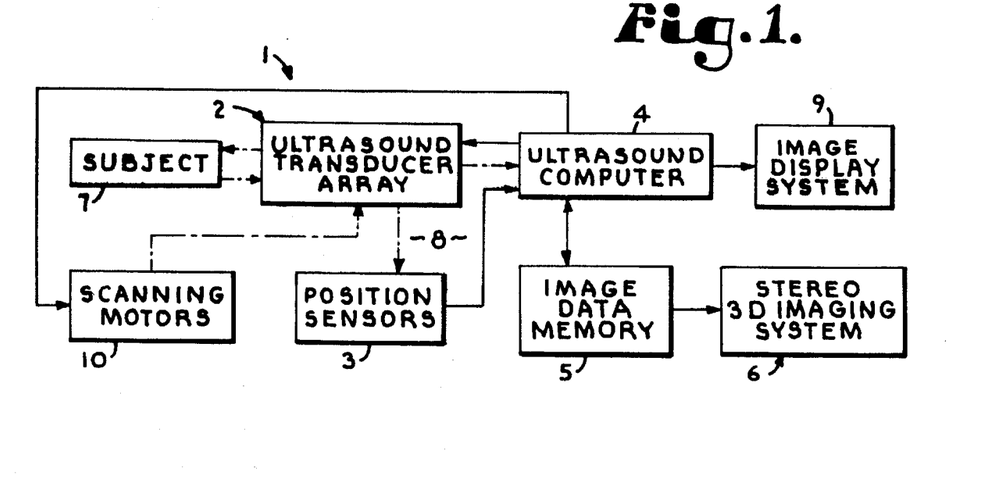
FIG. 1 is a simplified block diagram of a stereoscopically displayed three dimensional ultrasound imaging system embodying the present invention.

Referring to the drawings in more detail:

The reference numeral 1 generally designates a stereoscopically displayed three dimensional ultrasound imaging system embodying the present invention. The system 1 generally includes a two dimensional ultrasound transducer array 2, transducer array position sensors 3, ultrasound interface and control computer 4, image data storage or memory 5, and a stereoscopic three dimensional (3D) imaging subsystem 6. The array 2 is positioned on a patient or subject 7; scans are taken in a plurality of planes or slices; image data from the scans is stored in the image data memory 5; and the data is processed to construct three dimensional models from the slice data which are stereoscopically displayed by the 3D imaging subsystem 6. The array 2, position sensors 3, and ultrasound computer 4 constitute an ultrasound imaging apparatus 8 which may also include its own image display subsystem 9 and array positioning or scanning motors 10 associated with the array 2.

Figure 2:
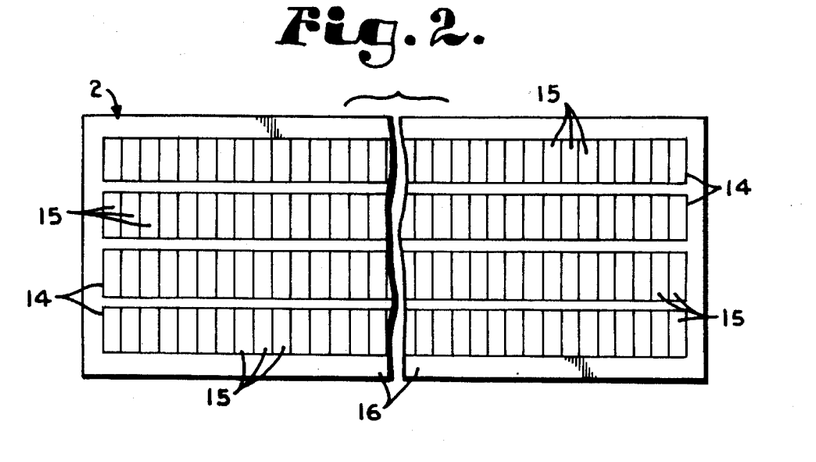
FIG. 2 is an enlarged diagrammatic bottom plan view of a two dimensional ultrasound transducer array for use in the system of the present invention.

FIG. 2 diagrammatically illustrates an exemplary ultrasound transducer array 2. The array 2 is formed of a plurality of rows 14 of individual ultrasound transducer elements 15. Each transducer element 15 is a piezoelectric crystal, such as lead zirconate titanate or the like, and has electrodes (not shown) in contact therewith which are electrically energized to cause the element to vibrate to thereby transmit sound energy therefrom. In medical sonography, the crystal or element 15 is subjected to a single voltage pulse and is allowed to vibrate at its natural resonant frequency which is determined by the physical dimensions of the crystal. Frequencies in the range of one to ten megahertz are useful in medical imaging. When an element 15 is vibrated by sound energy from an external source at a frequency within a given tolerance of its resonant frequency, the element 15 generates an alternating current electrical signal. Thus, each element 15 can be operated as a transmitter or receiver of sound energy.

The array 2 may be controlled by the ultrasound computer 4 in a manner similar to a stack of conventional linear transducer arrays. Such arrays typically include from 64 to 200 transducer elements, sometimes more, each element having a thickness of about one half millimeter. The elements 15 may be activated by the computer 4 in groups of individual elements to cause focusing of the ultrasound energy at selected depths and/or to aim the sound energy. As slice image data is obtained from exciting the elements 15 of one row 14 and receiving the energy therefrom, the next is similarly sequenced to obtain an adjacent image slice. The sound energy from the elements 15 may be focused to reduce the width of the beam in a direction along the length of the elements 15 (vertically, as viewed in FIG. 2) by conventional types of acoustic lenses. The ultrasound computer 4 may include conventional types of ultrasound controls, such as time gain compensation to strengthen echoes returning from greater depths, coarse gain controls to control the amplitude of all returning signals, reject controls to eliminate weaker return signals to thereby clarify the images, and the like.

The ultrasound transducer elements 15 are positioned in the rows 14 in a carrier block 16 which may be formed from a material such as polyethylene, polystyrene, silicone rubber, expanded polystyrene, or the like. The illustrated array 2 includes four rows 14 of transducer elements 15; however, greater or fewer numbers of rows 14 may be provided. The array 2 may be positioned on a patient 7 by hand for ultrasound imaging. Preferably, the array 2 is mounted in such a manner that its position may be sensed.

Figure 3:
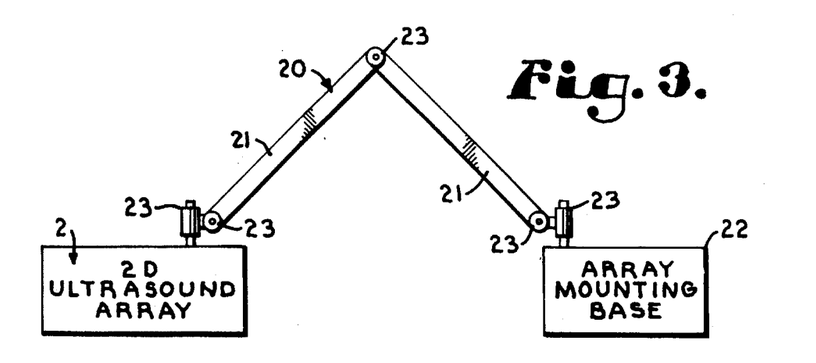
FIG. 3 is a diagrammatic side elevational view at a reduced scale of an articulated arm and a mounting base for the ultrasound transducer array of the present invention.

FIG. 3 illustrates an articulated arm 20 on which the ultrasound transducer array 2 may be mounted. The arm 20 includes several arm links 21 connected between the carrier block 16 of the array 2 and an array mounting base 22 by a plurality of joints of articulation 23. Each joint 23 includes a position sensor 3 whereby movement about or along an associated axis of articulation may be sensed and indicated to the ultrasound computer 4. By this means, image data derived by scans using the transducer array 2 may be located for reconstruction to a three dimensional model of the anatomical structures to be imaged.

Image data representing a plurality of slice images may be taken at each position of the array 2 relative to the patient 7. The array 2 is then moved to scan an additional plurality of slice planes. In order to better organize the process, the joints 23 of the arm 20 may be provided with the array positioning or scanning motors 10. The ultrasound computer 4 may control the motors 10 to position the array 2 in such a manner as to gather data from slice planes between those previously taken to increase the resolution of data obtained. The computer 4 is also capable of avoiding slice planes already imaged to speed the process. While the system 1 is illustrated in terms of the articulated arm 20, the array 2 may alternatively be supported by a motorized patient platform (not shown) the position of which is sensed by the position sensors 3 and the movement of which is controlled by the computer 4 to image a series of slice planes. Such a motorized patient platform may be similar to the types used in other types of imaging, such as computed tomography and the like. In the present invention, such an installation may also incorporate an articulated arm similar to the arm 20 but simplified to some degree.

Image data obtained by the ultrasound scans is stored in an ordered manner in the image data memory 5 and may be displayed monoscopically, a slice at a time, on the ultrasound image display 9.

Figure 4:
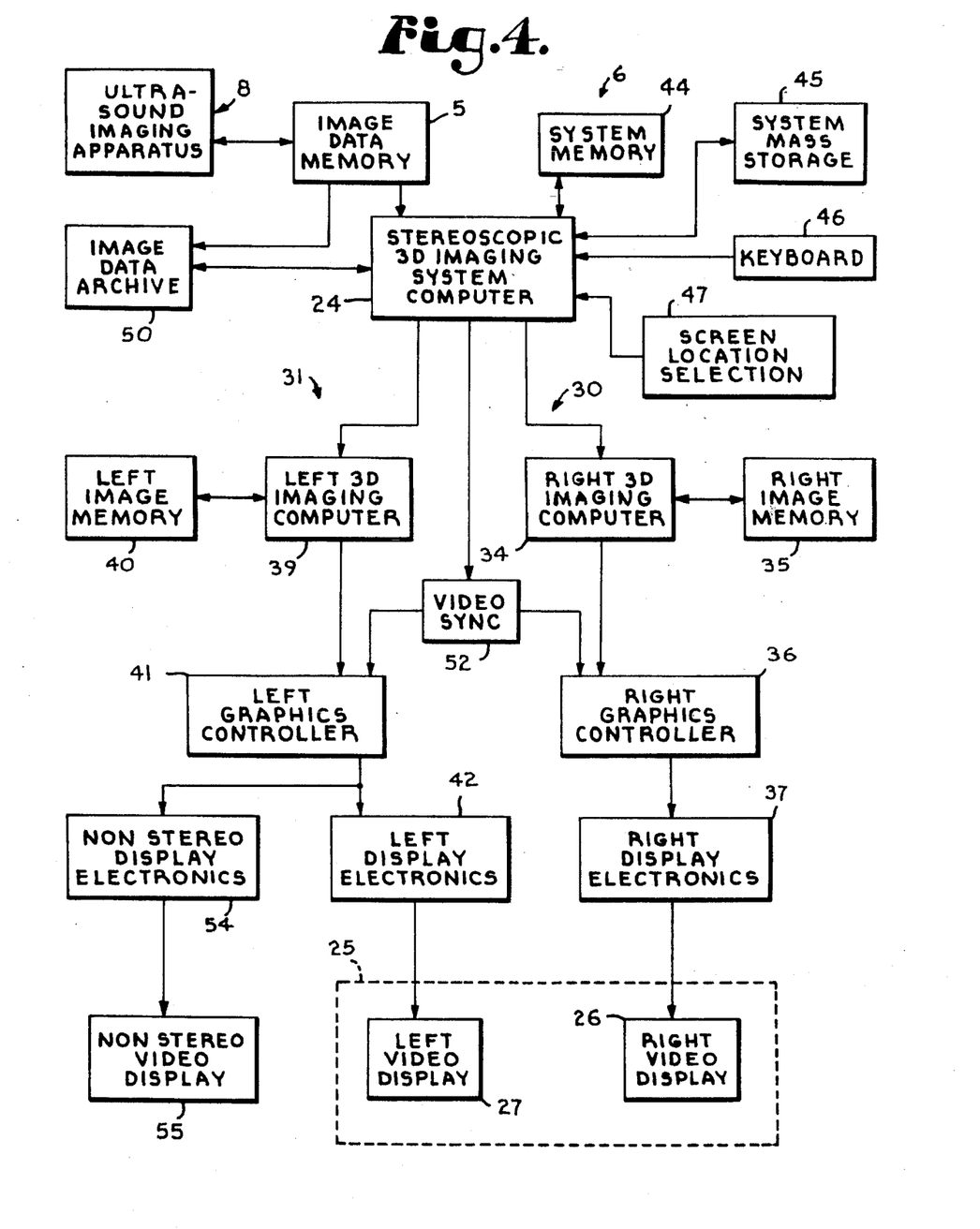
FIG. 4 is a block diagram illustrating the principal components of a stereoscopic three dimensional imaging apparatus for stereoscopically displaying images derived from ultrasound image data collected using the system of the present invention.

FIG. 4 illustrates the main functional blocks of the stereoscopic three dimensional imaging subsystem 6.

The reference numeral 6 generally designates a stereoscopically displayed three dimensional imaging system embodying the present invention. In general, the system 6 includes a stereoscopic three dimensional imaging system computer 24 which is interfaced between an ultrasound imaging apparatus 8 and a stereoscopic viewing unit 25. The system 6 receives image data generated by the imaging apparatus 8, reconstructs the image data into a three dimensional model, generates right and left stereoscopic three dimensional image components of the model, and displays the stereoscopic components on right and left video display devices 30 and 31 of the stereoscopic display or viewing unit 25 for viewing.

The system 6 includes right and left image channels 30 and 31 interfaced between the system computer 24 and the video display devices 26 and 27 respectively. The right image channel includes a right three dimensional display processor 34 and right video display device 26. Similarly, the left image channel 31 includes a left three dimensional display processor 39 and left video display device 27.

The system computer 24 includes CPU 43, system memory 44, system mass storage devices 45, a keyboard 46, and a screen location selection input 47. The mass storage devices 45 may include floppy disk drives and hard disk drives for storing an operating system and application programs for the system computer 24 and routines for manipulating the images displayed on the viewing unit 25 and for communicating with the imaging apparatus 8. The mass storage devices 45 may also store software for operating the 3D display processors 34 and 39. The keyboard 46 provides for command input to operate the system computer 24 to select image data sets to be displayed, for selecting image manipulation routines, and for required computer housekeeping activities. The screen location selection input or pointing device 47 may be a device such as a mouse, trackball, joystick, or the like for moving a cursor on the screens of the video display devices 26 and 27 to select areas of the displayed images to be manipulated or to select items from displayed menus for alternative command input.

The imaging apparatus 8 may be an implementation of the ultrasound imaging apparatus described above. The imaging apparatus 8 includes an image data memory 5 which stores data representing cross-sectional images of a patient during operation of the apparatus 8. The image data is stored more or less permanently in a non-volatile image data archive medium 50 which may be a computer tape system, a write-once laser disc, or the like. The system 6 may be interfaced to the imaging apparatus 8 directly or to the image memory 5 and receive image data in real time during the imaging of a patient. Alternatively, the system 6 may be interfaced to the image data archive 50 and obtain image data therefrom at some time after the actual imaging process generates the data and at a location remote from the imaging apparatus 3.

Each of the three dimensional display processors 34 and 39 is similar to conventional monoscopic three dimensional medical display processors which are available from several manufacturers and which are in operation in a number of hospital facilities. Such computers are similar in many respects to computer systems used for flight simulators in their ability to represent and manipulate three dimensional scenes. In three dimensional medical imaging computers, data is reconstructed from a series of slice images or tomographs to form a three dimensional model of the slices in a stacked sequence. In some cases, it is necessary to average or interpolate between actual image data points to enhance the resolution of the displayed image.

As stated earlier, system computer 24 is preferably of the type disclosed in U.S. Pat. No. 4,170,876. In this type of imaging system, voxel scanner 32 selects a set of eight cubically adjacent data points for processing. These data points are supplied to a comparator 33 which is also supplied with a threshold value or range of values. The comparator then generates an 8 bit vector which is used to address a polygon generator 35 which may be a read only memory containing an edge connecting polygon list. The referenced patent utilizes triangles but it should be clear that any desired polygon shape could be used. An interpolator 36 then performs an interpolation operation on each of the voxel elements to generate a polygonal surface approximation to the selected surface as represented by the threshold. This polygon list is then supplied to the left and right display processors 39 and 34, respectively. The display processors then generate vectors or raster format signals which are supplied to left and right video displays 27 and 26. For a more detailed description of the imaging system, see the above referenced patent.

Figure 11:
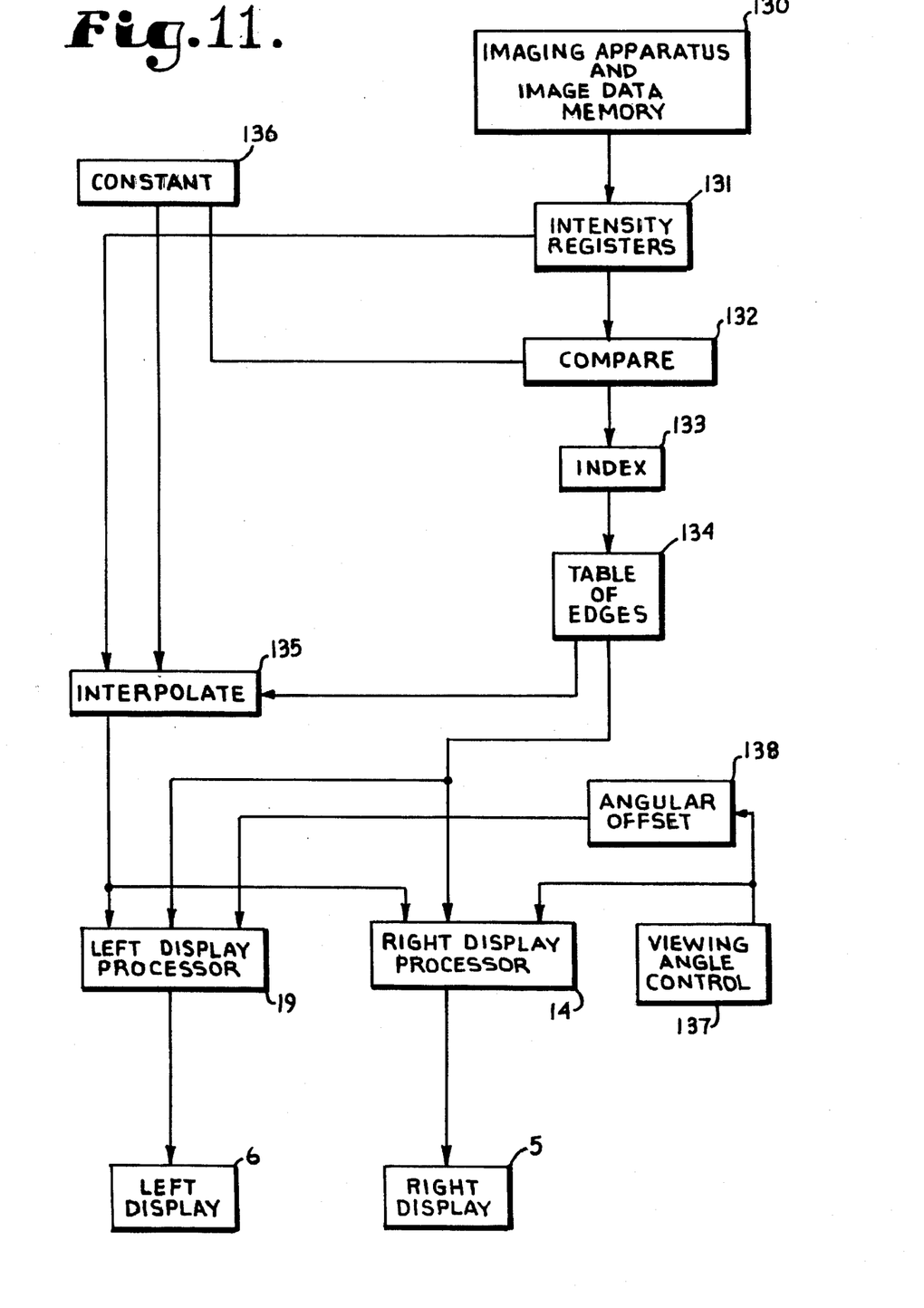
FIG. 11 is a flow chart illustrating data flow in the present invention.

A data flow diagram for the system is illustrated in FIG. 11. As explained in detail in the above referenced patent, voxel elements, each of which consists of 8 cubically adjacent data points, are loaded into intensity registers 131. These values are then compared with threshold values in comparison 132. The threshold values are constant with respect to each voxel. The comparison acts to generate an 8 bit vector which is used as an index to a table of edges at 133. An interpolation at block 134 is then performed utilizing the data from the edge table and the threshold and original voxel data to generate a polygon list representing a three dimensional tomograph. This list along with the date from the table of edges is then supplied to left and right display processors which generate vector or raster based 3 dimensional images. A control input from viewing angle and elevation control 137 is input to the processors, directly to one and offset by a calculated angle in the other to simulated stereoscopic image. The angle is calculated to simulate an approximate 2 inch spacing between the eyes of an ordinary observer at a selected view elevation. This angle can be calculated geometrically or can be accessed via a look-up table of angles and elevations. This calculation can be performed by a separate angle generator 48 as shown in FIG. 1 or directly by CPU 43. Surface shading is added in the display processors, depending on the orientation of a surface, to add visual clues which give the appearance of three dimensionality to the image. Color hues and densities are often assigned to the image data depending on the relative value range of the data. Alternatively, color may be assigned according to the known colors or idealized colors of the organs and anatomical structures represented.

The above features of conventional monoscopic 3D display processors provide a static view of anatomical structures. Such computers are also usually provided with software routines to allow manipulation of the images, such as rotation of the displayed image, removal of portions of the displayed anatomical structures to reveal other details, removal of superfluous details or portions, magnification of a selected portion of the structures, and the like.

Each of the 3D display processors 34 and 29 is conventional. The operation of the computers 34 and 39 is coordinated by the system computer 24 such that the images generated thereby form right and left stereoscopic components of the same three dimensional model via viewing angle control and offset angle generator 48 in FIG. 1. Again, this angle simulates spacing between an observer's eyes. Additionally, when the images are manipulated, CPU 43 assures that such manipulations occur in coordination within the 3D display processors 34 and 39. For example, if the displayed anatomical structures are to be rotated, rotation must occur at the same rate and about the same axes on both display devices 26 and 27. The system computer 24 also synchronizes the displays 26 and 27 by providing a master clock signal which is converted by a video synchronizing circuit 52 to a synchronizing trigger signal such that the sweep circuitry in the displays are synchronized.

Figure 12:
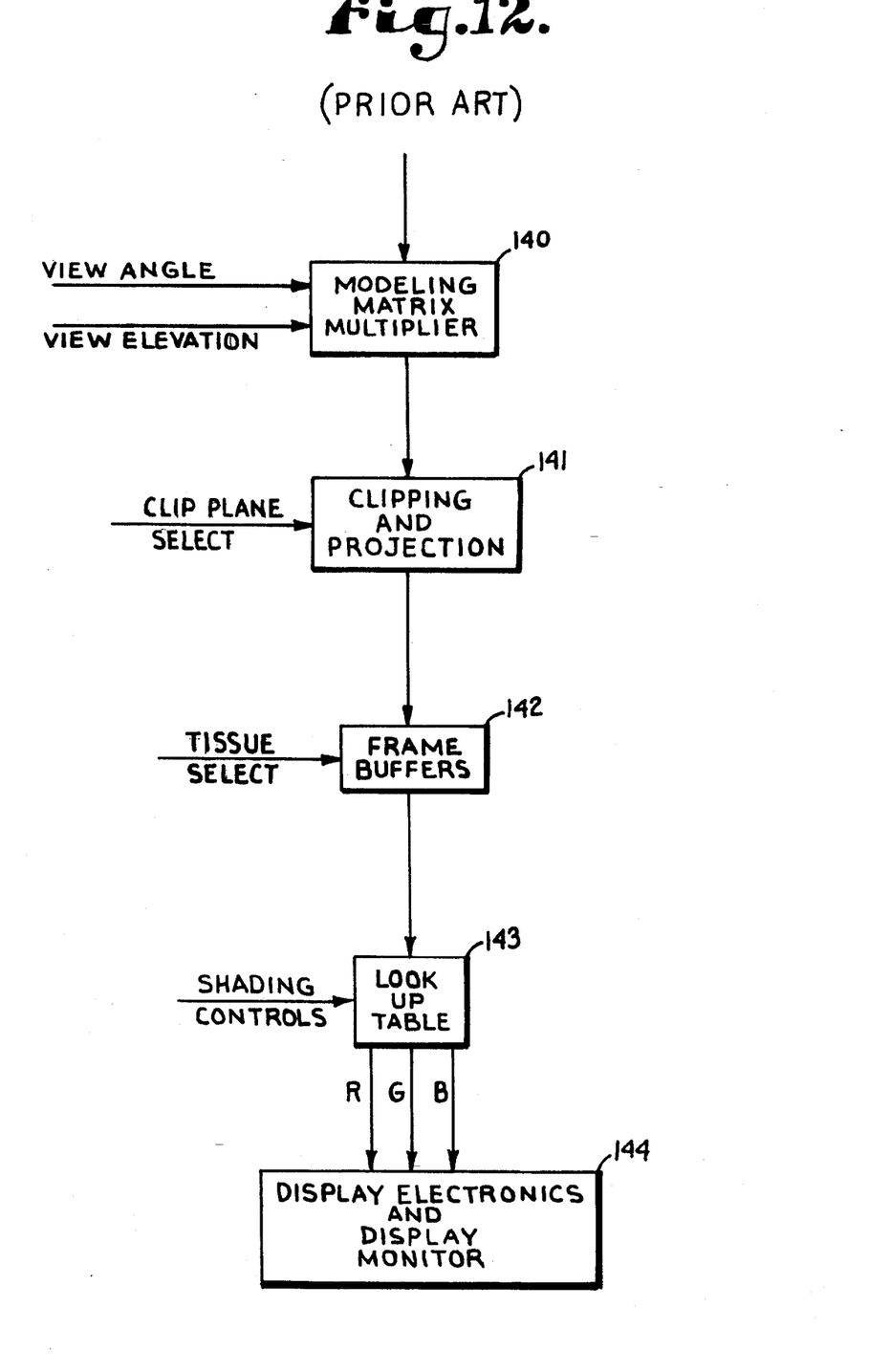
FIG. 12 is a block diagram illustrating the conventional principal components of one of the left and right display processors.

FIG. 12 illustrates a conventional display processor which could be utilized as the left and right display processors of the current invention. As earlier noted, such a processor is described in U.S. Pat. No. 4,719,585, to Cline et al., which is hereby incorporated by reference. In FIG. 14, polygon list information is loaded from system computer 24 of FIG. 4 into modeling matrix multiplier 140. View angle and elevation are supplied via a matrix multiplation in block 140. A conventional clipping is selectively performed in block 141 to generate crosssection image data. Overlapping images are stored in frame buffer(s) 142 and shading control and hidden surface removal are performed via look up table 143. The overlapping images, may, for example, represent bone structure, internal organs, and skin by selective use of different thresholds.

Preferably, at least one of the display processors, such as the left display processor 39, has an output for a nonstereoscopic display device 55. The display device 55 may, for example, be a large screen video monitor for monoscopically viewing of the images of the anatomical structures by a group of physicians or an assistant operating the system 6 at the direction of a physician viewing the images on the stereoscopic viewing unit 25.

Figures 5, 6:
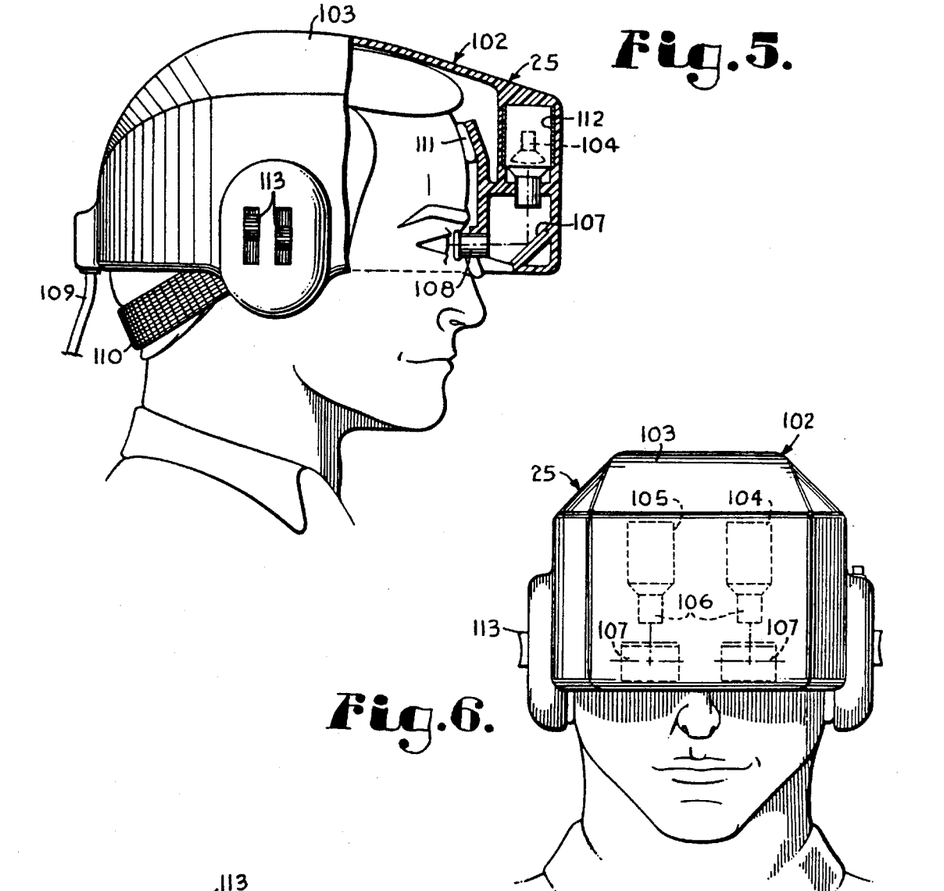
FIG. 5 is a side elevational view of a first stereoscopic display unit of the imaging system employing miniature cathode ray tubes as video display devices, with portions broken away to illustrate the optical elements which project a pair of images into the eyes of the viewer.
FIG. 6 is a front elevational view of the first display unit of the imaging system.
Figure 7:
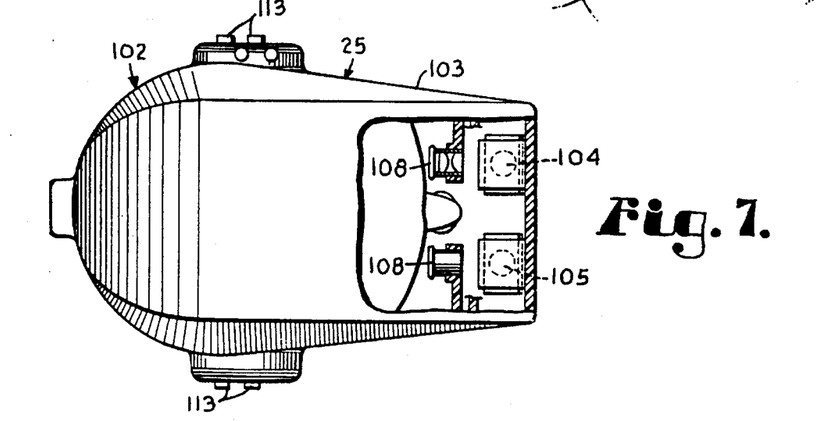
FIG. 7 is a top plan view of the first display unit with portions broken away to illustrate further details of the projection optics.

FIGS. 5–7 illustrate a first embodiment 102 of a head worn stereoscopic viewing or display unit 25. The unit 102 includes a cap or helmet 103 in which the components of the unit 102 are mounted. The right and left video display devices 26 and 27 are miniature color cathode ray tubes (CRT's) 104 and 105 respectively which are mounted within the helmet 103 for indirect projection of the images therefrom into the eyes of a person viewing the displays in order to decrease the possibility of projecting x-rays from the CRT's 104 and 105 into the eyes of the viewer.

The CRT's 104 and 105 are mounted for downward projection of the images thereof through projection optical elements 106 toward right angle reflecting elements 107 such as mirrors or prisms and from there through viewing lenses 108 to the eyes of the viewer. The viewing lenses 108 are provided to compensate for the short focal distance between the eyes of the viewer and the display devices 104 and 105 such that the images can be focused at a greater effective distance. The viewing lenses 108 are preferably finely adjustable to accommodate the visual capabilities of the eyes of the viewer. Further, the lateral positions of the right and left video display components are preferably adjustable to accommodate the spacing between the eyes of the viewer, although such adjustment means are not illustrated.

The video signals from the display electronics are provided to the components within the helmet 103 by a cable 109 which enters the unit 102 at the rear of the helmet 103. The helmet 103 preferably includes an adjustable harness for fitting the helmet to the head of the viewer, as represented by an elastic band 110. A forehead pad 111 is provided to maintain the position of the optical elements of the unit 102 in relation to the eyes fo the viewer. X-ray shields 112 are positioned to enclose the CRT's 104 and 105. The helmet 103 may be provided with controls 113 for adjusting characteristics of the images displayed on the CRT's, such as brightness and contrast.

Figures 8, 9:
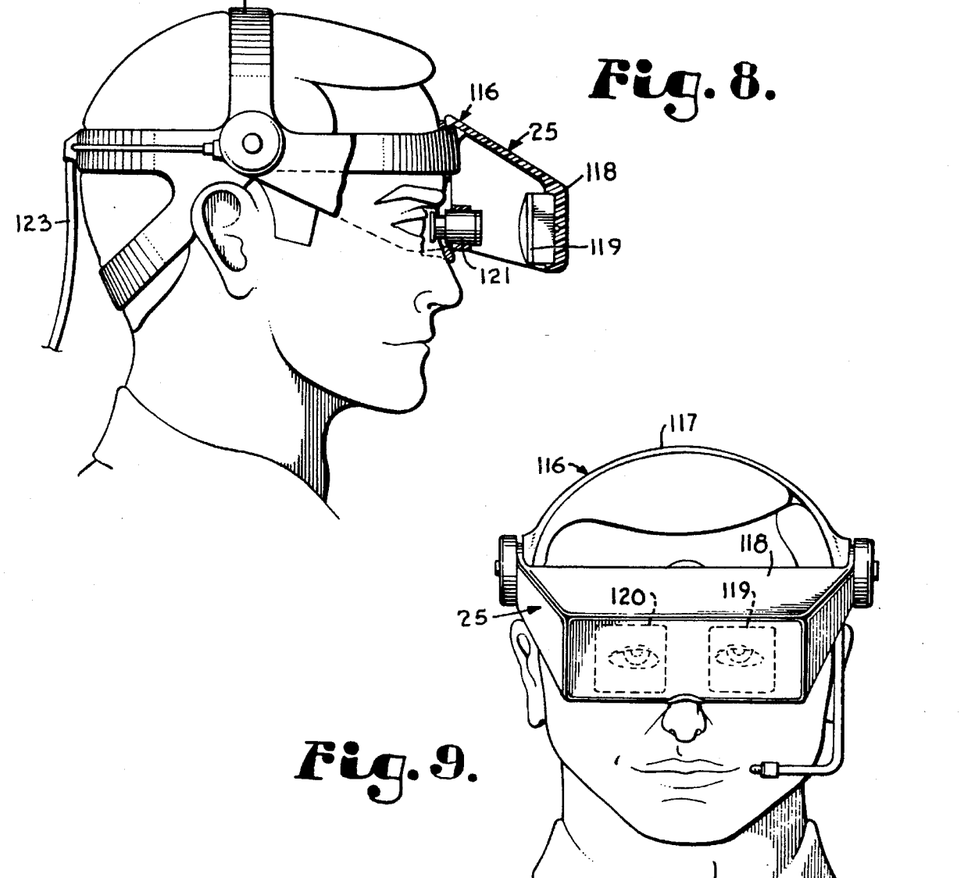
FIG. 8 is a side elevational view of a second stereoscopic display unit employing liquid crystal devices, with a portion broken away to illustrate details of the second display unit.
FIG. 9 is a front elevational view of the second display unit.
Figure 10:
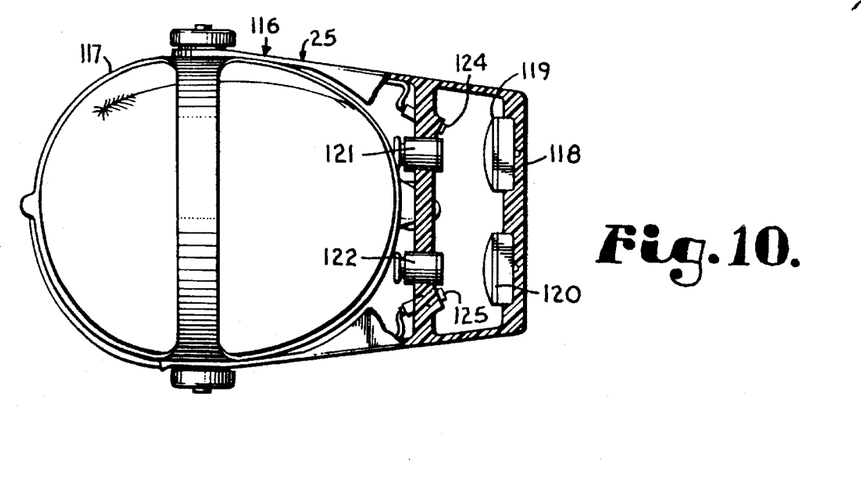
FIG. 10 is a top plan view of the second display unit with a portion broken away to illustrate internal details thereof.

FIGS. 8–10 illustrate a second embodiment 116 of the stereoscopic viewing unit 25. The unit 116 generally includes a support harness or headband 117 to which is pivotally connected a visor 118 having right and left video display devices 119 and 120 positioned therein. The harness 117 is preferably adjustable and is adapted for wearing on the head of a medical practitioner who is viewing the images generated by the system 1. In addition to the display devices 119 and 120, the visor 118 provides a mounting for right and left optical elements 121 and 122 which compensate for the close spacing between the video display devices 119 and 120 and the eyes of the viewer.

The illustrated right and left video display devices 26 and 27 are color dot matrix type liquid crystal displays (LCD's) 119 and 120. LCD's are much lighter in weight than cathode ray tubes, but their image resolution and color quality is currently not quite as good as comparably sized CRT's. LCD's are low voltage devices; thus, there is no problem of x-ray emissions therefrom. As a result, the LCD's 119 and 120 are mounted directly in line of sight of the eyes of the viewer. This results in a reduction in weight of the viewing unit 116 since mirrors or prisms are not required for reflecting the images.

It is desirable to mount a major portion of the display electronics, such as synchronization and sweep control circuitry, elsewhere than directly on the viewing unit 116 to keep the unit as light as possible. The display electronics are preferably mounted on a belt (not shown) worn by the practitioner such that the video signals are conducted to the display devices 119 and 120 by cables 123. The LCD's 119 and 120 do not radiate their own light and must be illuminated by separate sources. As illustrated, right and left light sources 124 and 125 are positioned within the unit 116 to illuminate the LCD's 119 and 120. Alternatively, backlight sources (not shown) may be provided behind the LCD's 119 and 120.

Although the head worn stereoscopic display units 102 or 116 are preferred, the stereoscopic viewing unit 25 may alternatively be adapted as a free standing unit-(not shown). Such a free standing unit would be designed along the same lines as the units 102 and 116 with less concern for weight.

It is to be understood that while certain forms of the present invention have been illustrated and described herein, it is not to be limited to the specific forms or arrangement of parts described and shown.

What is claimed and desired to be secured by Letters Patent is as follows:

1. A method of ultrasound imaging of anatomical structures of an organism comprising the steps of:
   (a) providing ultrasound energy;
   (b) propagating said energy through an organism having anatomical structures therein such that said energy is reflected from said anatomical structures;
   (c) receiving said energy after reflection from said anatomical structures;
   (d) measuring parameters of the reflected energy resulting from reflection from said anatomical structures;
   (e) converting said parameters to three dimensional image data representing images of said anatomical structures, said three dimensional image data comprising a range of shades of display color;
   (f) transforming said image data into independent, angularly displaced right and left three dimensional video signals representing right and left eye three dimensional stereoscopic components of an image of said anatomical structures from a first perspective, said transforming step including the steps of creating a three dimensional view from said first perspective of said three dimensional image data, said first perspective representing one of said right or left eye stereoscopic components and rotating said three dimensional image data from said first perspective to a second perspective and creating a second three dimensional view from said second perspective, said second perspective representing the other of said left and right eye stereoscopic components; and displaying said right and left stereoscopic components of said image on respective separate, independent right and left video displays to thereby provide a stereoscopic three dimensional view of said anatomical structures.

2. A method as set forth in claim 1 including the steps of:
   (a) positioning said right and left video display devices in a head worn viewing harness in which said right and left video display devices are supported by the head of a person viewing said images.

3. A method as set forth in claim 1 and further including the steps of:
   (a) causing said image of said anatomical structures as displayed to rotate about an axis from said first perspective to a third perspective; and
   (b) repeating said transforming step with said third perspective representing said one of said right or left eye views.

4. A method as set forth in claim 1 including the steps of:
   (a) correlating said range of shades of display color to a range of parameters of said energy as a result of reflection from said anatomical structures;
   (b) selecting an inhibition range of said shades of display color; and
   (c) causing the inhibition of the display of the inhibition range of said shades of display color to thereby enhance the view of remaining portions of said three dimensional image.

5. A method as set forth in claim 1 wherein:
   (a) said propagating and receiving steps include propagating said energy through said organism and receiving said energy in such a manner as to obtain said image data as a data array of spatially related image data points having values related to said parameters; and
   (b) said measuring and converting steps include interpolating to provide average image data point values between adjacent image data points to derive averaged image points interspersed among said image points to thereby create said three dimensional image.

6. A method as set forth in claim 1, wherein:
   (a) said propagating and receiving steps include propagating said energy through said organism and receiving said energy in such a manner as to obtain said image data in a form of a plurality of closely spaced and sequential two dimensional cross sectional images of a segment of said organism; and
   (b) said converting step includes assembling said image data in such a manner as to form a three dimensional model of said segment of said organism to thereby form said three dimensional image.

7. A method as set forth in claim 1 and further including the steps of:
   (a) storing said three dimensional image data;
   (b) recalling said three dimensional image data at a time remote from said generating step; and
   (c) performing said transforming and displaying steps on said recalled three dimensional image data.

8. A method of three dimensionally imaging anatomical structures of an organism using ultrasound energy and stereoscopically displaying images of said structures comprising the steps
   (a) providing said ultrasound energy;
   (b) propagating said ultrasound energy through an organism having anatomical structures therein such that said energy is reflected from said anatomical structures;
   (c) receiving said energy after reflection from said anatomical structures;
   (d) measuring parameters of said energy resulting from reflection from said anatomical structures;
   (e) converting said parameters to image data representing images of said anatomical structures, said image data comprising a range of shades of display color;
   (f) performing said propagating, receiving, measuring, and converting steps in such a manner as to obtain said image data in a form of a plurality of closely spaced and sequential two dimensional data arrays of spatially related image data points having values related to said parameters of said energy, said data arrays forming cross sectional images of a segment of said organism;
   (g) assembling said image data in such a manner as to form a three dimensional model;
   (h) transforming said three dimensional model into independent, angularly displaced right and left three dimensional video signals representing right and left eye three dimensional stereoscopic components of said three dimensional model from a first perspective, said transforming step including the steps of creating a three dimensional view from said first perspective of said three dimensional image data, said first perspective representing one of said right or left eye stereoscopic components and rotating said three dimensional image data from said first perspective to a second perspective and creating a second three dimensional view from said second perspective, said second perspective representing the other of said left and right eye stereoscopic components;

(i) providing a stereoscopic display unit including separate, independent right left video displays;

(j) displaying said right three dimensional model stereoscopic image component of a three dimensional image of said three dimensional model on said right video display; and (k) displaying said angularly displaced left three dimensional model stereoscopic image component of said three dimensional image of said three dimensional model on said left video display.

9. A method as set forth in claim 8 including the steps of:

(a) positioning said right and left video display devices in a head worn viewing harness in which said right and left video display devices are supported by the head of a person viewing said images.

10. A method as set forth in claim 8 and further including the steps of:

(a) causing said three dimensional model to rotate about an axis from said first perspective to a third perspective; and (b) repeating said transforming step with said third perspective representing said one of said right or left eye views.

11. A method as set forth in claim 8 including the steps of:

(a) correlating said range of shades of display color to a range of said parameters;

(b) selecting an inhibition range of said shades of display color; and (c) causing the inhibition of the display of the inhibition range of said shades of display color to thereby enhance the view of remaining portions of said image.

12. A method as set forth in claim 8, and further including the step of:

(a) interpolating said spatially related image data points to provide average image data point values between adjacent said spatially related image data points to derive averaged image points interspersed among said image data points.

13. A method as set forth in claim 8, and further including the steps of:

(a) storing said three dimensional model;

(b) recalling said three dimensional model at a time remote from said generating step; and (c) performing said transforming and displaying steps on said recalled three dimensional model.

14. An apparatus for stereoscopic ultrasound imaging of anatomical structures and comprising:

(a) ultrasound imaging means propagating ultrasound energy through an organism, receiving said energy as reflected from anatomical structures of said organism, measuring parameters of said energy as reflected from said anatomical structures, and converting said parameters to image data, said image data comprising a range of shades of display color;

(b) image data storage means interfaced with said imaging means and storing said image data;

(c) computer means interfaced with said image data storage means for receiving said image data, assembling said image data in such a manner as to form a three dimensional model of said segment of said organism, generating independent right and left eye angularly displaced three dimensional stereoscopic image data representing respective right and left stereoscopic component images of said three dimensional model by rotating said three dimensional model to yield respective right and left eye perspective components from a selected perspective view of said three dimensional model; and (d) stereoscopic display means interfaced with said computer means and including separate, independent right and left video displays, said display means receiving said right and left stereoscopic image data and transforming said into right and left video signals which are applied respectively to said right and left video displays to display said right and left stereoscopic component images respectively thereon.

15. An apparatus as set forth in claim 14 including:

(a) a viewing harness supporting said right and left video display devices on the head of a person viewing said images.

16. An apparatus as set forth in claim 14 wherein said computer means includes:

(a) right and left three dimensional display processors each receiving said three dimensional model image data and rotating said received image data in such a manner as to form a respective one of said right and left stereoscopic component images.

17. An apparatus as set forth in claim 16 wherein said computer means further includes:

(a) a system computer connected to said image data storage means and said right and left three dimensional display processors and providing said processors with said three dimensional model image data derived from said image data storage means, said system computer coordinating the operation of said right and left three dimensional display processors to display said right and left stereoscopic image components of said three dimensional model.

18. An apparatus as set forth in claim 14 wherein:

(a) said computer means is programmed to selectively cause said three dimensional model image data to rotate about an axis to allow stereoscopic viewing of said three dimensional image from a different perspective.

19. An apparatus as set forth in claim 14 wherein said computer means is programmed to:

(a) correlate said range of shades of display color to a range of variations in said parameters of said energy as a result of reflection from said anatomical structures;

(b) allow selection of an inhibition range of said shades of display color; and (c) selectively cause the inhibition of the display of the inhibition range of said shades of display color to thereby enhance viewing of remaining portions of said image.

20. An apparatus as set forth in claim 14 wherein:

(a) said imaging means propagates said energy through said organism and receives said energy in such a manner as to obtain said image data as a data array of spatially related image data points having values related to variations in said parameters of said energy; and (b) said computer means is programmed to:
  (1) interpolate said spatially related image data points to provide average image data point values between adjacent image data points to derive averaged image points interspersed among said image data points to yield said three dimensional model image data.

21. An apparatus as set forth in claim 14 wherein:
(a) said imaging means propagates said energy through said organism and receives said energy in such a manner as to obtain said image data in a form of a plurality of closely spaced and sequential two dimensional cross sectional images of a segment said organism; and
(b) said computer means is programmed to:
  (1) assemble said cross sectional images in such a manner as to form said three dimensional model image data of said segment of said organism.

22. An apparatus as set forth in claim 14 wherein said imaging means includes:
(a) a two dimensional element array of ultrasound transducers.

23. An apparatus as set forth in claim 14 wherein:
(a) said imaging means is operative to propagate and receive said energy in a scanned manner to thereby obtain said image data in a form of a plurality of closely spaced and sequential two dimensional data arrays of spatially related image data points having values related to said parameters of said energy, said data arrays forming cross sectional images of a segment of said organism.

24. An apparatus as set forth in claim 23 wherein:
(a) said computer means is programmed to assemble said two dimensional data arrays of spatially related image data points in such a manner as to form said three dimensional model image data of said segment of said organism.

25. An apparatus as set forth in claim 24 wherein said imaging means includes:
(a) a two dimensional element array of ultrasound transducers providing image data representing a selected plurality of cross sectional images of said organism;
(b) said element array and said organism being positioned for relative movement therebetween to provide image data representing a multiplicity of said plurality of cross sectional images of said organism; and
(c) array position sensing means coupled between said element array and said computer means, said array position sensing means sensing relative movement between said element array and said organism and providing a position signal to said computer means indicative of said relative movement whereby said computer means organizes said image data representing said cross sectional images of said organism for assembly into said three dimensional model of said segment of said organism.

26. An apparatus as set forth in claim 25 wherein said imaging means includes:
(a) array motor means operatively connected between said element array and said organism to cause selected relative movement therebetween.

27. An apparatus for stereoscopic ultrasound imaging of anatomical structures and comprising:
(a) ultrasound imaging means propagating ultrasound energy through an organism, receiving said energy as reflected from anatomical structures of said organism, measuring parameters of said energy as reflected from said anatomical structures, and converting said parameters to image data, said image data being in a form of a plurality of closely spaced and sequential two dimensional data arrays of spatially related image data points having values related to said energy, said data arrays forming cross sectional images of a segment of said organism;
(b) image data storage means interfaced with said imaging means and storing said image data;
(c) computer means interfaced with said image data storage means for receiving said image data and forming a three dimensional model of said image data, said computer means also generating independent right and left eye angularly displaced three dimensional stereoscopic image data representing respective right and left stereoscopic component images of said three dimensional model by rotating said three dimensional model to yield respective right and left eye perspective components from a selected perspective view of said three dimensional model;
(d) stereoscopic display means interfaced with said computer means and including separate, independent right and left video displays, said display means receiving said independent, angularly displaced right and left stereoscopic component images and transforming same into right and left video signals which represent said right and left stereoscopic component images, respectively;
(e) a right stereoscopic image component of a three dimensional image of said three dimensional model being displayed on said right video display; and
(f) an angularly displaced left stereoscopic image component of said three dimensional model being displayed on said left display.

28. An apparatus as set forth in claim 27 including:
(a) a viewing harness supporting said right and left video display devices on the head of a person viewing said images.

29. An apparatus as set forth in claim 27 wherein said computer means includes:
(a) right and left three dimensional display processors.

30. An apparatus as set forth in claim 27 wherein said imaging means includes:
(a) a two dimensional element array of ultrasound transducers providing image data representing a selected plurality of cross sectional images of said organism;
(b) said element array and said organism being positioned for relative movement therebetween to provide image data representing a multiplicity of said plurality of cross sectional images of said organism; and
(c) array position sensing means coupled between said element array and said computer means, said array position sensing means sensing relative movement between said element array and said organism and providing a position signal to said computer means indicative of said relative movement whereby said computer means organizes said image data representing said cross sectional images of said organism for assembly into said three dimensional model of said segment of said organism.

31. An apparatus as set forth in claim 30 wherein said imaging means includes:
(a) array motor means operatively connected between said element array and said organism to cause selected relative movement therebetween.

* * * * *